United States Patent
Aggarwala (10) Patent No.: US 7,963,654 B2
(45) Date of Patent: Jun. 21, 2011

(54) APPARATUS AND METHOD FOR SUBJECTIVE DETERMINATION OF THE REFRACTIVE ERROR OF THE EYE

(76) Inventor: Karan Aggarwala, Haryana (IN)

( * ) Notice: Subject to any disclaimer, the term of this patent is extended or adjusted under 35 U.S.C. 154(b) by 95 days.

(21) Appl. No.: 12/445,416

(22) PCT Filed: Oct. 16, 2007

(86) PCT No.: PCT/IN2007/000483
§ 371 (c)(1),
(2), (4) Date: Apr. 13, 2009

(87) PCT Pub. No.: WO2008/047385
PCT Pub. Date: Apr. 24, 2008

(65) Prior Publication Data
US 2010/0007850 A1    Jan. 14, 2010

(30) Foreign Application Priority Data
Oct. 16, 2006   (IN) .......................... 2266/DEL/2006

(51) Int. Cl.
*A61B 3/02* (2006.01)
*A61B 3/00* (2006.01)
(52) U.S. Cl. .................... 351/224; 351/237; 351/246
(58) Field of Classification Search .......... 351/224–226, 351/237–239, 246
See application file for complete search history.

(56) References Cited

U.S. PATENT DOCUMENTS

| | | | | |
|---|---|---|---|---|
| 3,758,201 A | * | 9/1973 | MacNeille | 351/232 |
| 4,105,303 A | * | 8/1978 | Guyton | 351/246 |
| 4,408,846 A | * | 10/1983 | Balliet | 351/203 |
| 4,618,231 A | | 10/1986 | Genco et al. | |
| 5,237,351 A | | 8/1993 | Kohayakawa et al. | |
| 5,450,145 A | * | 9/1995 | Valentine | 351/243 |
| 5,675,399 A | | 10/1997 | Kohayakawa | |
| 2004/0041980 A1 | * | 3/2004 | Laguette et al. | 351/243 |

FOREIGN PATENT DOCUMENTS

EP    1649802 A1    4/2006

OTHER PUBLICATIONS

International Search Report issued in PCT/IN2007/000483, mailed on Mar. 3, 2008, 3 pages.
Written Opinion issued in PCT/IN2007/000483, mailed on Mar. 3, 2008, 6 pages.

* cited by examiner

*Primary Examiner* — Jordan M. Schwartz
(74) *Attorney, Agent, or Firm* — Osha • Liang LLP (57) ABSTRACT

The invention provides for a subjective refractor for determining refractive error of the eye comprising an optical system for presenting at least two targets to the eye, the difference of focus between the targets greater than the predicted depth of focus of the eye; —means for indicating target preference from the presented targets; and means for determining refractive error of the eye on the basis of target preference.

16 Claims, 7 Drawing Sheets

Figure 7

APPARATUS AND METHOD FOR SUBJECTIVE DETERMINATION OF THE REFRACTIVE ERROR OF THE EYE

The present invention relates to an apparatus and method for subjectively determining the refractive power of the human eye.

DESCRIPTION OF RELATED ART

Determining the refractive error of the eye for eyeglass prescription requires skill and is prone to errors. When one focuses upon a target of interest, the target of interest is sharply focused upon the retina of the eye. From the point of best focus, when the target is moved away from the eye until it just starts to blur, the far edge of the depth of field is determined. The near edge of the depth of field is somewhat more difficult to estimate. When the target of interest is moved from the point of best focus toward the eye until it first stimulates accommodation or when it just starts to blur, whichever comes first, the near edge of the depth of field is determined. To determine depth of focus, the dioptric equivalent of the far edge and the near edge of the depth of field are determined as the reciprocal of the distance to the nodal point of the eye in meters and the smaller number is subtracted from the larger number to obtain the total depth of focus in diopters.

Environmental conditions being constant, depth of focus is determined by two factors, the pupil diameter and the visual resolution or contrast discrimination ability of the eye in the region of retina being stimulated by the target of interest. When visual resolution is poor, or when pupil diameter is small, depth of focus increases. On the other hand, when visual resolution is good and when pupil diameter is increased, depth of focus decreases. Thus an eye with 6/6 visual resolution and a large 7 mm pupil is likely to have a very small depth of focus. On the other hand, an eye with 6/18 visual resolution and a small pupil of 2 mm is likely to have a large depth of focus. Good visual resolution means smaller changes can be detected, making depth of focus smaller. Poor visual resolution means only large changes in blur are noticed, thereby increasing depth of focus.

Conventional subjective refraction techniques practiced in an examination lane aim to place the far edge of the depth of field on the Snellen chart at a distance of 6 meters, thereby approximating optical infinity. While such techniques do not explicitly use the concept of depth of focus, they may do so indirectly in the hands of an experienced examiner.

Subjective refractors typically require active participation by an operator. Of those that do not require significant operator participation, problems related to visual accommodation or focusing effort by the subject exist. Furthermore, problems relating to visualization of small alphanumeric characters of a display chart also continue to exist, especially for subjects with media opacities such as cataract or central visual anomalies such as macular degeneration. Finally, subjects with small pupils, or large depth of focus, continue to be a challenge for previous subjective refractors.

Subjective refraction is a challenge in many clinical environments and research facilities for various reasons. First, reimbursement from managed care networks is less for refraction compared to other clinical procedures. Increased subject volume in urban or suburban communities produces managerial difficulties. Eye-care practitioners who specialize in a certain field say glaucoma or retina or vision research may have insufficient time or expertise for refraction. Such busy eye-care practitioners mostly ophthalmologists but also some optometrists may delegate refraction to a poorly trained technician whose results may be questionable. Second, some subjects are difficult to examine by objective refractors because of media opacities such as cataract, corneal dystrophy, or reduced pupil size in older subjects, or those taking miotic medication for glaucoma. Third, some subjects with central visual anomalies are difficult to refract as they have reduced foveal visual acuity, or enlarged depth of focus, and are unable to visualize or distinguish the focus of the small characters of the Snellen chart upon which they are required to fixate. Fourth, many subjects suffer from accommodative anomalies and significant examiner skill or cycloplegia (pharmaceutical paralysis of the ciliary muscle) are required.

SUMMARY

The teachings of this document provide for the minimization of the use of an operator skilled in the art of refraction. The document also provides for an apparatus and method for refraction that minimizes the problems associated with visualizing small alphanumeric characters, small pupils or large depth of focus, insufficient time for refraction or visual accommodation.

The invention relates to a subjective refractor for determining refractive error of the eye comprising an optical system for presenting at least two targets to the eye, the difference of focus between the targets greater than the predicted depth of focus of the eye; —means for indicating target preference from the presented targets; and means for determining refractive error of the eye on the basis of target preference.

The subjective refractor comprises meridian altering mechanism for presenting at least two targets to the eye along at least two meridians of the eye. The subjective refractor comprises means for presenting at least two targets to the eye along at least two orientations.

The optical system of the subjective refractor presents at least two targets simultaneously to one eye such that the targets are juxtaposed or presents at least two targets successively to one eye such that the targets are presented sequentially The subjective refractor comprises focus altering means for altering focus of presented targets. Either all targets are focused by the focus altering means or one target is fixed.

The predicted depth of focus maybe calculated by the visual acuity and pupil diameter of the eye. The predicted depth of focus maybe multiplied by a factor greater than one. The light forming the targets preferably has a bandwidth less than 160 nm and preferably more than 20 nm and has wavelength in the range of 500 nm to 700 nm.

The invention provides for a method of determining the refractive error of the eye comprising presenting at least two targets to the eye, the difference of focus between the targets greater than the predicted depth of focus of the eye, receiving target preference feedback, and determining the refractive error based on the target preference feedback.

The invention also relates to a system for determining the refractive error of the eye comprising: an optical system for presenting at least two targets to the eye, the difference of focus between the targets greater than the predicted depth of focus of the eye, a means for indicating target preference from the presented targets; a focus altering means altering the focus of presented targets; and a data management system for receiving target preference input and determining the refractive error of the eye.

The system comprises an accommodative pattern detector and an accommodative pattern compensator for determining and compensating over accommodation by an eye based on the target preference input.

DESCRIPTION OF THE PREFERRED EMBODIMENTS

For the purpose of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated system, and such further applications of the principles of the invention as illustrated therein being contemplated as would normally occur to one skilled in the art to which the invention relates.

It will be understood by those skilled in the art that the foregoing general description and the following detailed description are exemplary and explanatory of the invention and are not intended to be restrictive thereof.

The method, apparatus and system of the present invention determines the refraction of an eye subjectively by interaction with the subject, under minimal supervision, by measuring at least two refractive meridians of the eye. The interactive subjective refractor presents at least two images to the eye, which differ in focus by an amount that exceeds the depth of focus of the eye. These images are compared for clarity or sharpness by the subject. The subject indicates preference of one image over the other or indicates that the two images appear equally clear or equally blurred. On receiving the subject's input the system presents a new pair of images based on the subject's prior response. If the subject prefers a 'farther' target image indicating a relatively 'plus power' light vergence, the system repositions both target images in the direction of the preferred focus. This process iterates according to an adaptive positioning sequence until a range of refractive limits and an endpoint are estimated.

The apparatus and system automates the process of subjective refraction so that after initial data input, alignment, and instruction, the subject can be minimally supervised until the refraction of one eye is determined. The apparatus may either be portable and mountable on a standard ophthalmic diagnostic instrument or it may have its own instrument table.

In its preferred embodiment, the optical system employed by the apparatus of the present invention includes a Badal lens that allows a wide range of optical distances to be represented within the space of two or more focal lengths from the Badal lens. The Badal lens is chosen so that its second focal plane is in the nodal plane of the subject's eye, approximated by the entrance pupil of the eye. The advantage of a Badal optical system is that changes in target position are linearly related to changes in dioptric focus.

The optical system is used to present two targets or target images to one eye of the subject. The targets are separated along the optical axis of the lens by an amount that exceeds the total depth of focus of the eye. The difference in focus between the two targets "delta"[δ] is referred to as inter target difference of focus. When viewed by the subject, the targets appear located adjacent to one another and one target usually appears more focused than the other. In physical space, the targets need not be physically adjacent to each other, so long as they are optically juxtaposed. Thus, optical juxtaposition can be attained by physical adjacency in a large field lens, or by the use of a bipartite mirror, or pairs of orthogonal mirrors and a beam splitter. Various types of optical systems have been described in the prior art and other literature, and some of these may be employed so long as they offer a sufficiently large field of view.

Using a Badal optical system, if position of the lens is chosen so that its second focal plane is in the nodal plane of the subject's eye, then if x is the displacement of the target from the first focal plane of the lens in meters, $$xx'=f^2 \qquad \text{Equation (1)}$$

f(=1/F) is the focal length of the lens in meters and x' is the distance in meters between the image of the target and the nodal plane of the subject's eye. If the distance x' is expressed in terms of its reciprocal R, the foregoing equation (1) becomes $$R=xF^2 \qquad \text{Equation (2)}$$

Here F is the dioptric power of the Badal lens—a constant under conditions of use—and x is the distance in meters between the target and the first focal plane of the lens in Equation 2. R is the dioptric distance between the image of the target and the nodal plane of the subject's eye and is the measure of the change in refractive power that is required to focus the target sharply on the subject's retina. It is important to note that in a Badal system, R is a linear function of the displacement x of the target and the retinal image size and often the retinal illuminance of the target are independent of R.

Mainly two types of Badal configuration have been described in the literature, one in which the back focal point of the convex lens coincides with the nodal point (or pupil plane) of the eye, and another in which the back focal point of the convex lens falls in the spectacle plane of the eye. Either configuration is acceptable because if the pupil plane configuration is chosen, later adjustments to the final prescription can be made to refer the resulting prescription to the spectacle plane.

The optical system may employ images of the targets in accessory telecentric lenses instead of the physical targets themselves or a movable thin prism may be employed to alter optical path length. Alternatively, a pair of right-angled mirrored prisms may be used to alter optical path length.

In using the interactive subjective refractor of the present invention, as opposed to conventional subjective refraction, the reaction time of the subject is less important, because of simultaneous presentation of the test targets. Thus, the subject need not rely on the memory of a blurred target instead an immediate comparison of clarity is made possible. This has the effect of reducing the time required for completing a monocular subjective refraction by nearly a factor of two in many cases. In addition, automation of the procedure for subjective refraction allows the examiner to momentarily perform other duties while the subject interfaces with the device. A complete standardization of the subjective refraction procedure also will allow minimally trained personnel to conduct the test and obtain reliable results.

For the proposed method of comparative subjective refraction to work effectively, the inter target difference of focus should be equal to or greater than the predicted depth of focus of the eye. This means that the two targets must appear visibly different from one another in sharpness. Depth of focus of the eye in subjects with normal visual capabilities and a pupil size of 3 to 5 mm is usually less than 0.50 D (±0.25 D). In subjects with somewhat reduced vision such as from early cataract or other pathology depth of focus is larger than normal and the inter target difference of focus must be at least 1.00 D to allow testing of individuals with somewhat reduced vision.

Similarly, in subjects with pupils of diameter less than 3 mm, depth of focus is larger than normal. Subjects with a pupil diameter of 2 mm and otherwise normal visual acuity are likely to have a depth of focus of about 0.75 D. Thus, to allow testing of subjects with somewhat reduced visual acuity, as well as for testing subjects with pupils of diameter less than 3 mm, it is advisable to present targets that differ in focus by about 1.00 D. The use of a 1.00 D diopter inter target difference of focus rather than smaller differences thus ensures that one of the two targets will be perceived as sharper than the other by a wide range of individuals, thereby increasing the probability of a response that is consistent with the state of focus of the eye, and reducing the probability of responses based on chance.

While determining the refractive error, accommodation of the eye should also be accounted for. Methods for controlling accommodation have been incorporated into the interactive subjective refractor.

Figure 1:
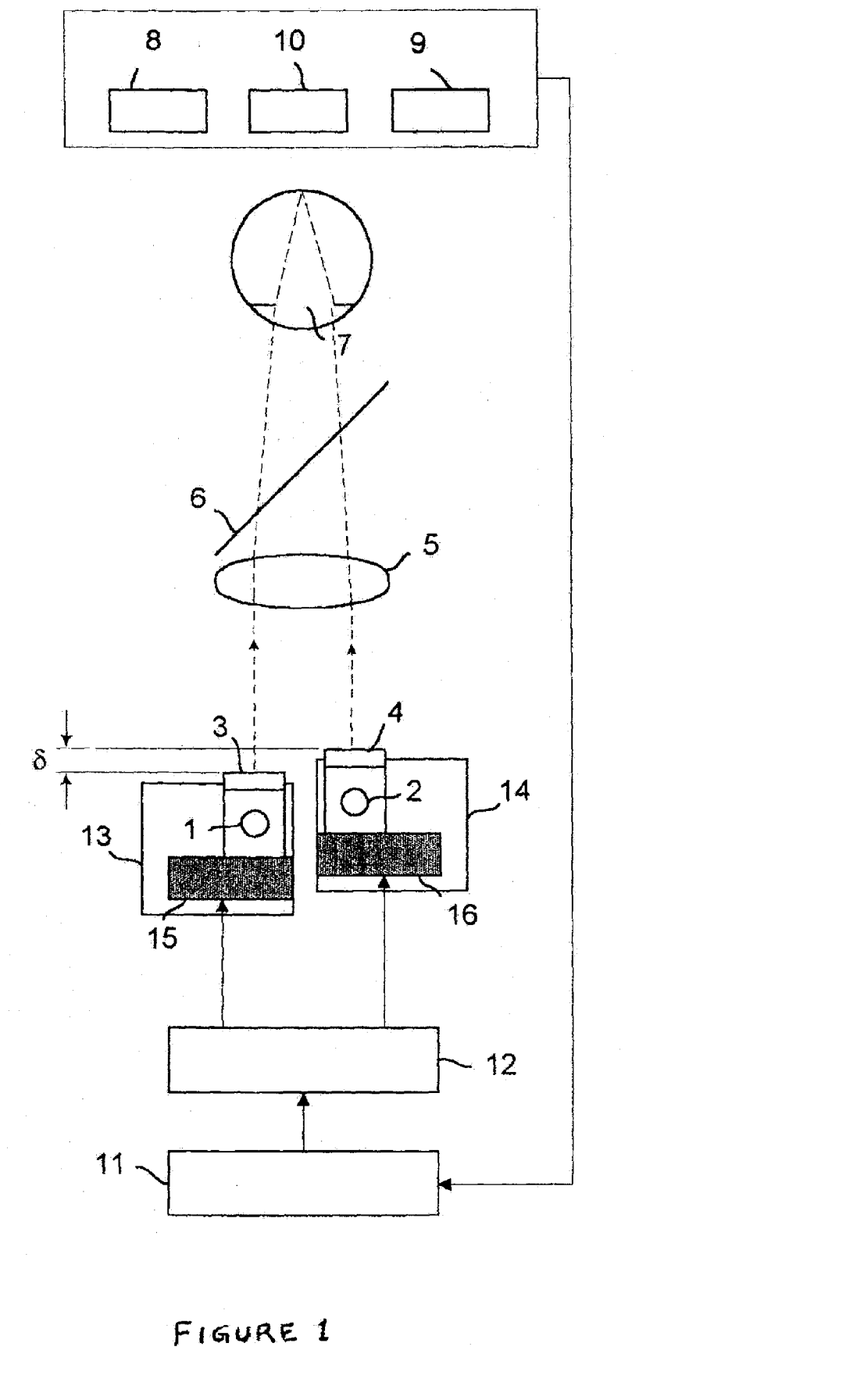
FIG. 1 is a schematic representation of the subjective refractor.

As shown schematically in FIG. 1, the apparatus or interactive subjective refractor of the present invention comprises of two identical sources of illumination (1, 2). In the preferred embodiment the illumination system may be composed of light-emitting diodes. In an alternate embodiment, the illumination system may be a white-light source and the longitudinal chromatic aberration of the human eye may be minimized by a band-limited spectral filter or by a specially designed achromatizing lens. The apparatus comprises a "right hand side" target pattern 3 and a "left hand side" target pattern 4, which may be identical to the right hand side target pattern 3, except it may be focused closer to or farther away from the lens by a certain amount. The inter target difference of focus may usually range from 0.5 D to 2.0 D.

The apparatus comprises of a beam splitter 6 that allows a camera or other imaging device to locate the pupil plane of the subject's eye, and facilitate mechanical alignment of the interactive subjective refractor of the present invention with the pupil plane.

The pupil plane 7 of the eye has been illustrated and for all practical purposes, the nodal point of the eye lies at the pupil plane and the interactive subjective refractor of the present invention would be aligned and focused so that the pupil plane is at a distance of one focal length from the Badal lens.

When the target images are compared for clarity, the subject has the option to indicate which target appears clearer, by way of subject input switches. For example, switch 8 may be used for indicating that image 3 is clearer, and switch 9 may be used for indicating that image 4 is clearer. If both images appear equally clear or equally blurred, the subject may press the central or "neither target" switch 10.

Figure 7:
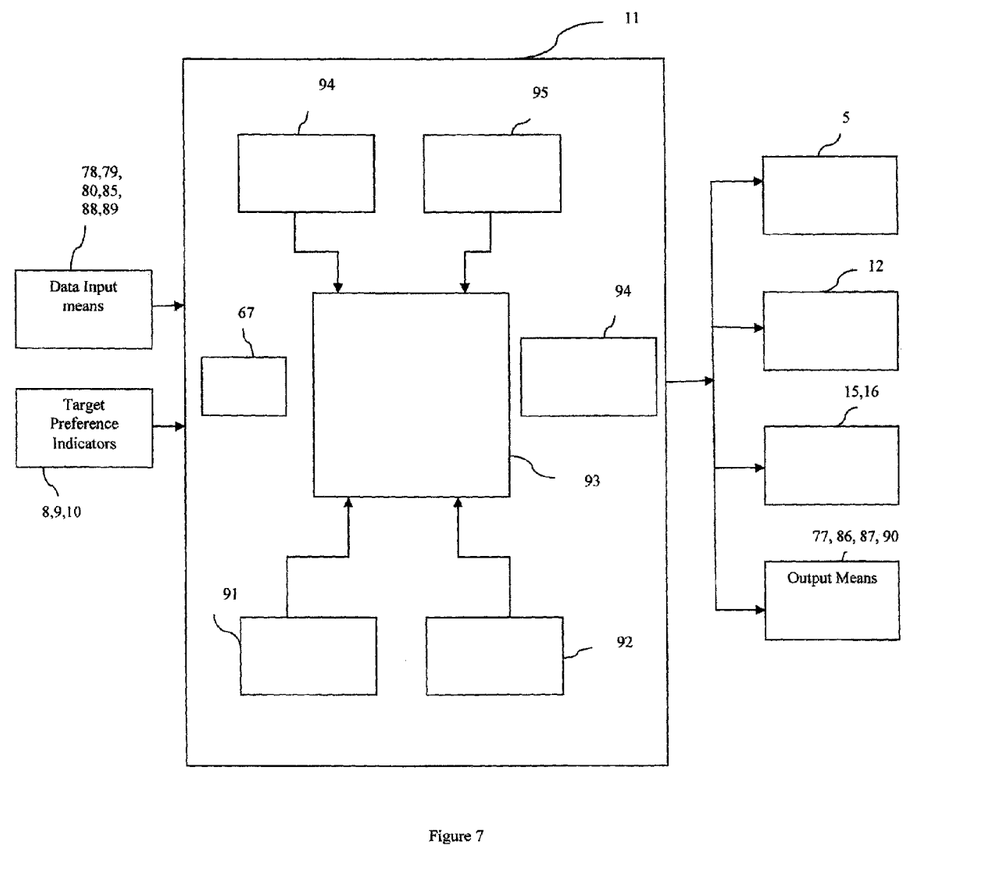
FIG. 7 illustrates a system for determining the refractive error of the eye.

Responses from the input switches are received by the system (11) as illustrated in FIGS. 1 and 7, which control a stepper motor (12), or other appropriate means, to change the focus of the target images by way of focus altering means. In the present example the means may be a linear motion mechanism (13, 14). When the refraction for one meridian is determined, the target images are moved by way of any suitable meridian altering mechanism to present targets along different meridians. In the present example the mechanism may be a rotating mechanism (15, 16).

With reference to the accompanying drawings, to begin the refraction, the subject is seated comfortably on a stool or a chair near the apparatus of the present invention, which is located on an adjustable instrument table or other adjustable mount. The optical system of the apparatus of the present invention is aligned and focused upon the plane of the entrance pupil (7) of one eye of the subject. The alignment mechanism preferably includes a means for viewing the eye, such as a photocell or a video camera (23) coupled to a display (24), a 3-axis adjustable instrument base (83), operated by a joystick (81) and toroidal control (82) or other manual or automated alignment mechanism, a chin rest (17), and a forehead rest (18). The subject's previous eyeglass prescription or starting refraction is approximately entered into the apparatus of the present invention, using 'plus' (78) or 'minus' (79) switches, while the subject looks into the apparatus. Approximate clarity of the targets is thus obtainable even if the subject's previous eyeglass prescription is unknown or non-existent. Following attainment of approximate clarity, the enter data button (80), is engaged. A liquid crystal display (LCD, 77) or other display means serves as a status indicator to inform the operator of the dioptric position of the targets, to ask a question, to display a result, or to present an error or miscellaneous message. Other subject data may also be input into the apparatus of the present invention, including eye being measured (right or left), the subject's age, and approximate pupil diameter as observed using reticule (84) and prior best corrected visual acuity and change since prior refraction. These data may also later be used by the apparatus of the present invention to estimate the subject's accommodative strategy or pattern and to compensate for it. The apparatus is provided with an on-off switch (75), and recalibrate switch (76). A method for increasing the range of refractive errors measurable by the apparatus may include placing a lens in the spectacle plane whose power is later added to the spherical component of the final refraction.

After initial data entry, alignment and instruction, the subject takes control of the input switches (8, 9, 10), by way of which target clarity preference is indicated and the refract switch (85) is engaged. Results are provided by way of the means for display such as alphanumeric LCD (77), a printer (86), USB data port (87), or audio output (90).

Additional interaction between the apparatus of the present invention and the operator is attainable by way of questions asked by the apparatus of the present invention via the LCD (77), to which the operator responds by way a 'yes' switch (88) or a 'no' switch (89).

The subject is instructed that they will be looking at two targets (3, 4), and they are required to compare the focus (clarity, sharpness, or degree of blurredness) of the two targets. On comparison, they will be required to indicate which of the two targets appeared more focused or less blurred, by engaging a switch, one for each target (8, 9). If both targets appear equally clear or equally blurred, they are instructed to engage a third switch (10). To start the refraction, the 'refract' switch (85) is engaged on the instrument panel.

A pair of targets or target images that differ in focus by an amount that is larger than the approximate depth of focus of the eye is presented. The pair of targets is presented as separated in space, though a time-based separation can be considered in an alternate embodiment. When the subject selects one target as more focused, in the presentation that follows, a pair of targets are presented that have an optical vergence (focus) that is dioptrically offset "or stepped" by a certain amount usually between 0.25 and 2.00 D, toward the subject's preference. Once again the subject makes a selection, and if the choice is biased toward the same direction as the previous choice, targets are dioptrically offset to follow the subject's choice.

The presentation of successive targets based on previous target preferences is achieved by focus altering means (94). This may be achieved by (a) physical movement of the targets in free space; (b) physical movement of the targets within an optical viewing system composed of a single lens or a plurality of lenses (e.g. a Badal optical system); (c) movement of an optical image of each target in free space; (d) movement of an optical image of each target within said optical viewing system. (e) Lenses placed close to the eye or imaged close to the eye (e.g. in the spectacle plane) or in the pupil plane. (f) the use of combinations of cylindrical lenses to alter focus; (g) a movable aperture within an optical system; (h) a gradient index lens with variable circular aperture or multiple annular apertures; (i) use of a radially symmetric curved mirror or plurality of mirrors. In an alternate embodiment, there may be one large mechanical system for moving both targets together, and one smaller mechanical system mounted on top of the larger system, to reposition only one of the two targets. Instead of the natural right-left dichotomy, in an alternate embodiment, the target patterns may be displaced vertically, one above the other.

This process continues until the subject selects a target that is biased in a direction opposite to the subject's preference in the preceding trial. When such a selection occurs (termed as a 'reversal'), it is duly recorded within the memory (67). The refraction continues until a specified number of reversals occur, a minimum of 2 but as many as 7, contingent on other parameters, including the amount of step size. On completion of the specified number of reversals, if the historical record of the subject's responses shows relative consistency, the refraction for the meridian being tested is calculated based on a measure of central tendency and displayed. If there is some inconsistency, the accommodative pattern compensator (91, 92) acts on the data to produce the first meridional endpoint, which is stored in memory (67). Third-quartile sampling of the range of acceptable target focus positions may be used as a bias-compensator for accommodation. The third quartile has a slightly more positive value than the midpoint of the range, and this ensures that the far edge of the depth of field of the eye is conjugate with the target. This type of refraction is called hyperfocal refraction, and is the goal of conventional subjective refraction procedures.

These cycles of operation continue until it becomes apparent to the system that the subject's responses appear to reposition the targets close to a position on the linear motion scale in a way that positions some distance closer to the lens are repeatedly rejected and some positions farther away from the lens are repeatedly rejected. The near limit and far limit of the target positions that are rejected by the subject are determined by the system based on the recent history of the subject's responses stored in memory (67). The mean position is then determined and the third quartile of the range or some other number obtained by available data is stored in memory. The accommodative pattern detector and compensator access the stored pattern of subject preferences and combine them with inputted data such as age and pupil diameter, and produce a meridional endpoint for each target orientation. This represents the refraction of the tested eye for one target orientation.

Following determination of the first meridional endpoint, the apparatus of the present invention immediately reorients the targets to a second meridian and the subject proceeds to make selections of perceived target focus as above.

The refraction procedure may be repeated for a third target orientation. If the data from the three target orientations appear to have minimal variability in range of reversals and meridional endpoint value, and if the computed astigmatism is low, it may not be necessary to test a fourth target orientation. If, however, variability or computed astigmatism exceeds a criterion value, a fourth target orientation will be presented by the apparatus of the present invention.

Refraction is computed by the meridional synthesis module (95) in terms of spherical and astigmatic components based on the results for the three, four or more tested meridians. This computation may be conducted by any known method such as that described in the paper "Simplified Analysis of Meridional Refraction Data" by Worthey, published in the American Journal of Optometry and Physiological Optics, Vol 54, 1977. The historical record of the subject's responses is analyzed by the apparatus of the present invention and is interpreted by the accommodative pattern detector (91) to reflect the degree to which the subject's responses represent reliable outcomes. This record is also made available for operator analysis, upon request. If the historical record is characteristic of a particular accommodative disorder, disorder of depth of focus, or other anomaly, a message to indicate the possible presence of such a disorder is displayed.

Visual acuity and pupil diameter are used by the system to compute predicted depth of focus in diopters based on a standard formula (Borish, 1971). A multiplier is used upon the predicted depth of focus to serve as a buffer so as to ensure that the unknown actual depth of focus is exceeded by the inter target difference of focus. This multiplier can by way of example be considered to be the numeral 2. The starting refraction is entered by the operator based on prior eyeglasses or based on a prior objective test such as skiascopy. The starting refraction is used to position the targets or target images (3, 4) in such as way that the nearer or more minus target (4) represents the refractive power in the most hyperopic (plus lens power) meridian of the starting refraction. The farther target (3) is positioned at a dioptric vergence of delta from the most myopic meridian. If the starting refraction is not known, then the targets are positioned equally on either side of optical infinity. Subject age in years is entered by the operator. Change in refraction between two prior refractions separated by a one year interval is entered if known. Subject age and change in refraction are used by the accommodative pattern detector (91) along with subject inputs (8, 9, 10) to compensate for any tendency for over-accommodation by way of the accommodative pattern compensator (92). The output of the accommodative pattern compensator is used by the data management system (93) to control the focus altering means (94) which controls position of the two targets (3, 4) and their inter target difference of focus.

When either best corrected visual acuity or pupil diameter or both are not available, the predicted depth of focus is taken to be 1.00 D. If the eye under test has no pathology, its total depth of focus will be about 0.50 D. In accordance with an embodiment, the focus altering means and its control during the refraction of any one meridian may be as follows:

1. Present targets separated by double the predicted depth of focus 2(DOF). This dioptric separation between the targets (inter-target difference of focus or δ is designated as $δ_1$.
2. Assume that the starting refraction is not known, thereby the targets (3,4) are positioned equally on either side of optical infinity.

3. If the subject prefers the more plus power target (3), move both targets together in the plus power direction by step size $\delta_1=\delta_1=2(DOF)$. If the subject prefers the more minus power target (4), move both targets together in the minus power direction by step size $S_1=\delta_1=2(DOF)$.
4. If the subject prefers neither target it suggests that the targets are far away from the final refraction or that the target vergence difference is smaller than the actual depth of focus of the eye under test. Thereby, the selection of the "neither" subject input switch (10) invokes the data management system (93) in concert with the accommodative pattern detector (91) and compensator (92) to expand (e.g. double) the value of the inter target difference of focus so that $\delta_2=2\delta_1$.
5. The trial continues as described in the above steps 3 or 4 until the preferred target reverses. A reversal of target preference constitutes either change from preferring the more minus target (4) to the more plus target (3) or a change from preferring the more plus target (3) to the more minus target (4).
6. After the initial doubling of the inter target difference of focus ($\delta_2=2\delta_1$), subsequent engagement of the "neither target" subject input switch (10) does not further expand inter target difference of focus, instead the accommodative pattern detector (91) and compensator (92) assume that the two targets appear equally blurred or equally clear to the eye not because of a very large depth of focus but because the targets (3, 4) are positioned on opposite sides of the meridional endpoint. If, however, the subject continues to engage the "neither target" switch (10), an error message is displayed indicating to the operator that the subject cannot be refracted until the inter target difference of focus is appreciable. If this happens, the operator can either enter a new starting refraction or reinstruct the subject.
7. Following the first reversal, so long as the "neither target" subject input switch (10) is not engaged, step size (S1) is halved so that $S_2=S_1/2$.
8. The targets move together in the direction of the preferred target (plus or minus) until a second reversal occurs. At second reversal, step size is further halved so that $S_3=S_2/2=S_1/4$.
9. With step size of 0.25 when two reversals occur, the trial halts and the dioptric interval (also called "range") between the two preferred targets preceding a reversal is divided into 4 parts and the absolute value of the $3^{rd}$ quartile is added to the more minus or less plus dioptric vergence to obtain the refractive endpoint for the tested meridian. Alternatively, the most plus preferred lens is determined and half the depth of focus is subtracted from the most plus preferred lens to yield the meridional endpoint.

Whereas the midpoint of two positions that the subject preferred may be used, instead, the $3^{rd}$ quartile in the direction of more positive (plus) power will be used. This ensures that the refractive endpoint is one at which the subject's accommodation is relaxed and the far edge of the depth of focus of the eye lies close to optical infinity. This is the basis for hyperfocal refraction, and forms the ultimate goal of standard refractive procedures employed by eye-care practitioners.

An example demonstrating the operation of iterative target positioning assuming that the desired meridional endpoint equals minus 2.00 D:
1. Assume that the predicted depth of focus equals 0.5 D. The starting inter-target difference of focus ($\delta_1$) is set to 0.5×2=1.00 D.
2. Assume that starting refraction was not entered and the targets are thereby positioned equally on either side of optical infinity.
3. The following sequence of target vergence presentations is likely to occur.

|   | Left target (more − D) | Right target (more + D) | Preferred input | Action |
|---|---|---|---|---|
| 1 | −0.50 | +0.50 | Left (9) | Move targets in the minus direction by 1.00 D. |
| 2 | −1.50 | −0.50 | Left (9) | Move targets in the minus direction by 1.00 D. |
| 3 | −2.50 | −1.50 | Left (9) | Move targets in the minus direction by 1.00 D. |
| 4 | −3.50 | −2.50 | Right (8) | At first reversal, step size halved. Move targets in plus direction by 0.50 D. |
| 5 | −3.00 | −2.00 | Right (8) | Move both in plus direction by 0.50 D. |
| 6 | −2.50 | −1.50 | Left (9) | At second reversal, step size halved. Move targets in minus direction by 0.25 D. |
| 7 | −2.75 | −1.75 | Right (8) | At third reversal, step size is halved only if step size S3 is > or = 0.50 D. |
| 8 | −2.50 | −1.50 | Left (9) | The number of reversals is counted after the step size has reached 0.25 D. |

When the number of reversals with step size 0.25 D reaches 2, the most plus preferred lens is determined. In this example it is −1.75. Half of the depth of focus is subtracted from the most plus preferred lens to determine the meridional endpoint. Thus the endpoint is −2.00. The endpoint may alternatively be determined using the range of preferred lenses determined after the step size reaches 0.25 D. The $3^{rd}$ quartile of the absolute value of the range is added to the more minus preferred lens (−2.50). This yields the result of −2.50+0.5625=−1.9375, which when rounded to the nearest 0.25 is −2.00.

It is noteworthy that the mean starting point for the next refractive meridian will not be optical infinity, instead it will be one diopter more plus than the last tested meridian. This is likely to reduce the number of trials for subsequent meridians, particularly for high refractive errors.

Figure 2:
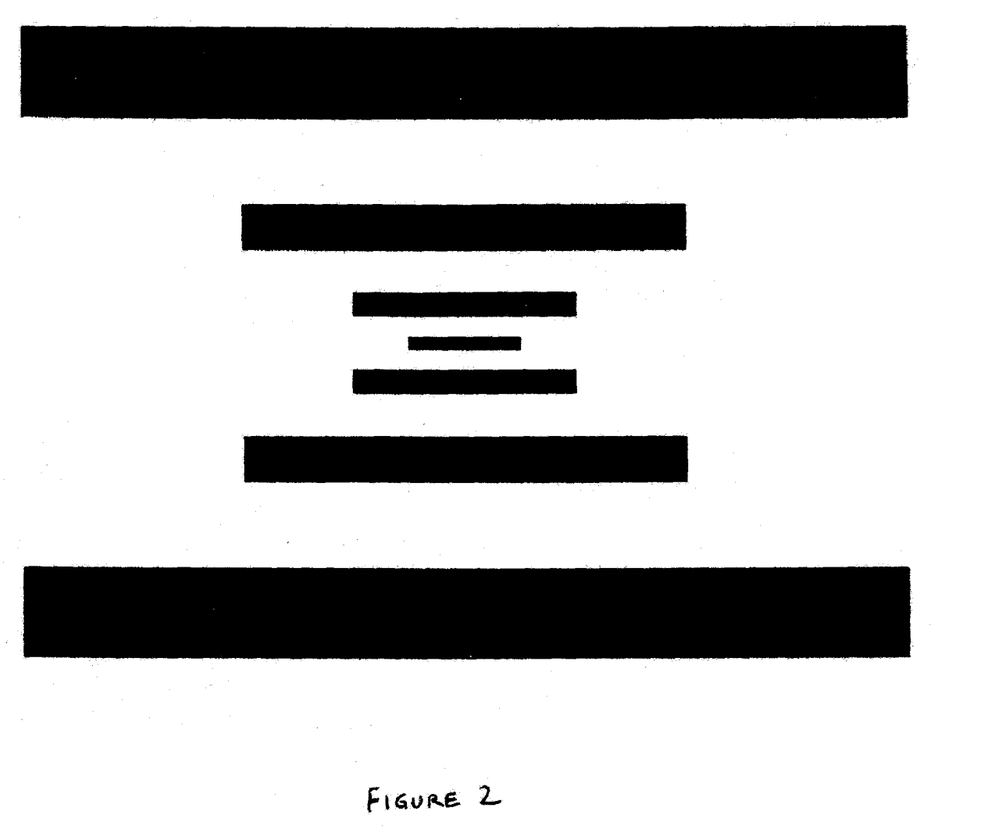
FIG. 2 is a pictorial representation of a target image.

As may be seen in FIG. 2, the target comprises parallel linear elements of various sizes arranged to simulate a scene with geometrical perspective. Whereas the preferred embodiment drawn in FIG. 2 shows discrete lines, texture elements may be used instead of lines. The ratio of length to width of the lines in FIG. 2 is about 10:1, but other ratios ranging from 5:1 to 20:1 may be employed to achieve a similar effect. The line-width in FIG. 2 may be proportional to visual acuity levels on the Snellen chart. In another embodiment, the center of the target could have a pair of linear elements or multiple linear elements. In another embodiment the lines may not correspond to Snellen ratios so long as they simulate geometrical perspective.

The target in the interactive subjective refractor of the present invention optical system is such that it allows isolation of at least two refractive meridians of the eye. In the preferred embodiment, it is composed of a pattern of parallel linear elements that can be rotated to determine the refraction for each of at least three meridians. Measures of refraction for predefined meridians are incorporated into the system (11) to determine the complete spherical refraction and astigmatic refraction of the eye. Accommodation is controlled by special target design that simulates a scene with geometrical perspective, by narrow-band illumination or an achromatizing lens that reduces longitudinal chromatic aberration to partially disable neural sensory mechanisms that control accommodation, by adaptively varying the order of presentation of the targets to compensate for the subject's age-related accommodative strategy, and by third quartile sampling of the range of refractive limits in the determination of the endpoint.

Whereas all the linear elements in FIG. 2 are parallel to each other, another embodiment may include a small percentage of linear elements that are not parallel to the remaining majority of linear elements. For example the center of the target may contain mutually orthogonal linear elements making the appearance of a square, rectangle, 'x', or a cross. However, this is contingent on the presence of a perceived geometrical perspective maintained by the presence of the remaining parallel linear elements. Thus, the target may include some characters or combinations of linear or curved elements that do not follow the general trend of linear elements of progressively smaller size from outer to inner parts of the target so long as the presence of those non-parallel or non-linear elements does not preclude the overall perception of geometrical perspective.

When the subject views the center of each target, the brain will be perceptually cued or fooled into believing that the center of the target is some distance away from the subject. Such a powerful perceptual cue for depth relaxes the accommodative mechanism of the eye, encouraging it to focus toward optical infinity. Such focusing toward optical infinity prevents over-correction of myopia and similarly prevents under-correction of hyperopia that may have otherwise resulted from excess accommodation.

Figure 3:
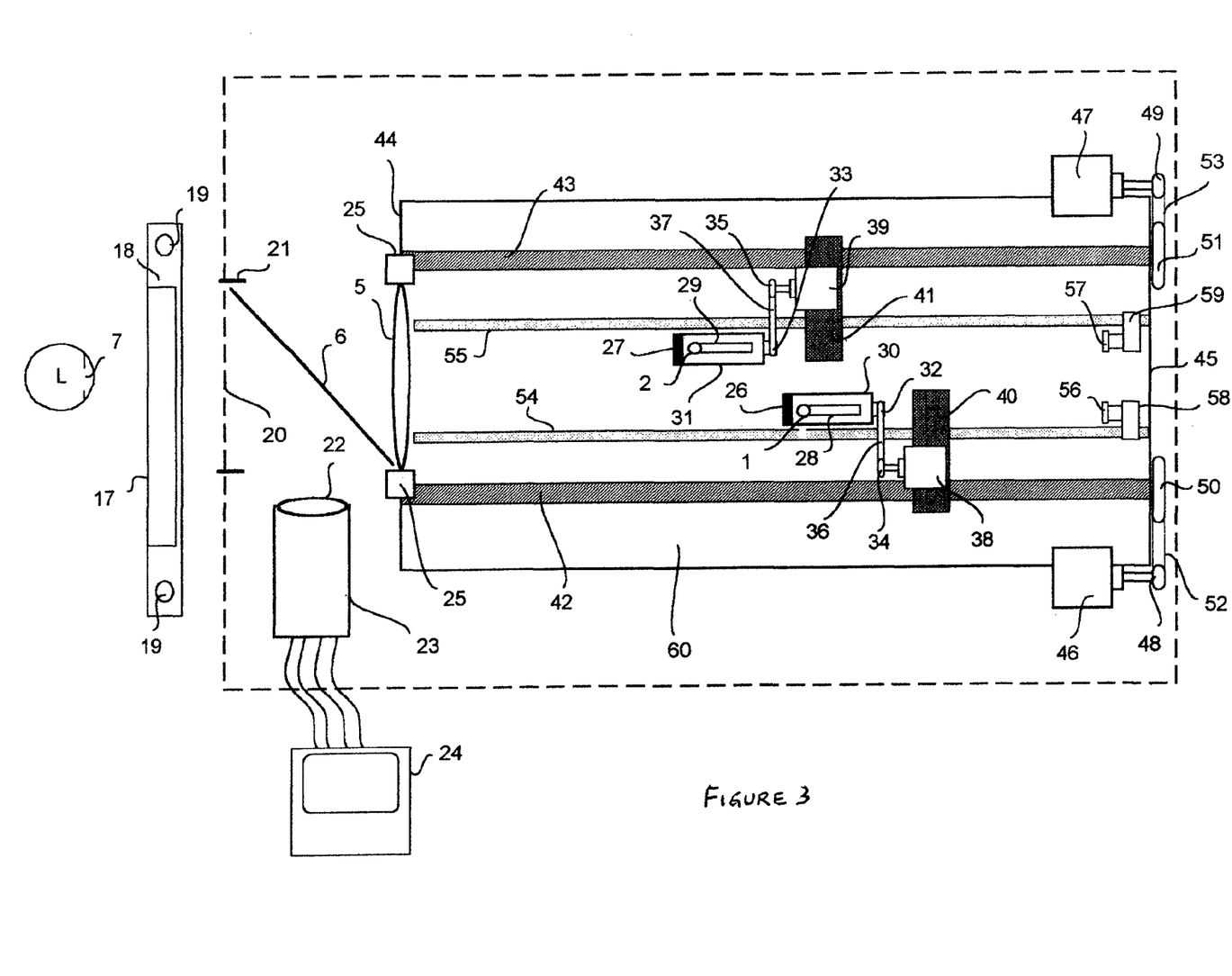
FIG. 3 is a schematic representation of the subjective refractor in top plan.

A schematic view of an embodiment of the apparatus is presented in FIG. 3. The instrument is aligned and focused upon the pupil plane of one eye, with the aid of a chin rest, a forehead mount, and head support assembly (19), by manipulating the chassis using a joystick (81) and toroidal manipulator (82). The subject looks into the apparatus through a flat glass plate (20), mounted within a large aperture (21). A beam splitter (6) allows visualization of the subject's eye by way of a focusing lens (22), a charge coupled device (CCD) camera or photocells (23), and a display monitor (24). The optical system (5) such as a Badal lens is mounted within the apparatus in a lens mount (25), and it receives patterns of light (3, 4) from the target surfaces (26, 27). The subject is thus able to view the meridional pattern target surfaces (26, 27), illuminated by light emitting diodes (LEDs) (1, 2), thus observing laterally displaced images of FIG. 2 that differ in focus.

The LEDs (1, 2) are mounted in stems (28, 29), which are encapsulated within rotatable drums (30, 31). Means for rotation, such as planetary gears (32, 33) are mounted upon the rotatable drums (30, 31). The planetary gears (32, 33) are rotatable by satellite gears (34, 35), via rotational belts (36, 37), driven by rotational stepper motors (38, 39).

The figures and the corresponding description discuss the system employing a Badal lens as the optical system for presenting targets. Accordingly, the figures illustrate linear adjustments to implement change in target focus. It would however be apparent to a person in the art that the teachings as described herein may be applied to any other means for iteratively adjusting the focus of the targets.

As shown in FIG. 3, the LEDs (1, 2), and parts 27 through 39 are mounted upon linearly movable carriages (40, 41), each of which are independently translatable along the optical axis of the Badal lens (5), by the action of lead screws (42, 43), the ends of which are rotatable within a front plate (44) and a back plate (45). Linear stepper motors (46, 47), drive the lead screws (42, 43) by way of solar gears (48, 49), galactic gears (50, 51), and linear belts (52, 53). Guide rods (54, 55) stabilize the travel trajectory of the linearly movable carriages (40, 41). In an alternate embodiment, lead screws and gears may be replaced by other means for translating targets such as a sliding mechanism encoded magnetically or optically or some other linear motion mechanism.

During the initial boot-up or the re-calibration process of the apparatus, the carriages (40, 41) are individually driven toward the back plate until they engage linear limit switches (56, 57). The linear limit switches (56, 57) are mounted in adjustable mounts (58, 59), upon their respective guide rods (54, 55). The front plate (44) and back plate (45) are fixedly mounted upon the main optics mounting plate (60). In an alternate embodiment, the linear position of the carriages may be electronically encoded along the entire length of travel.

Figure 4:
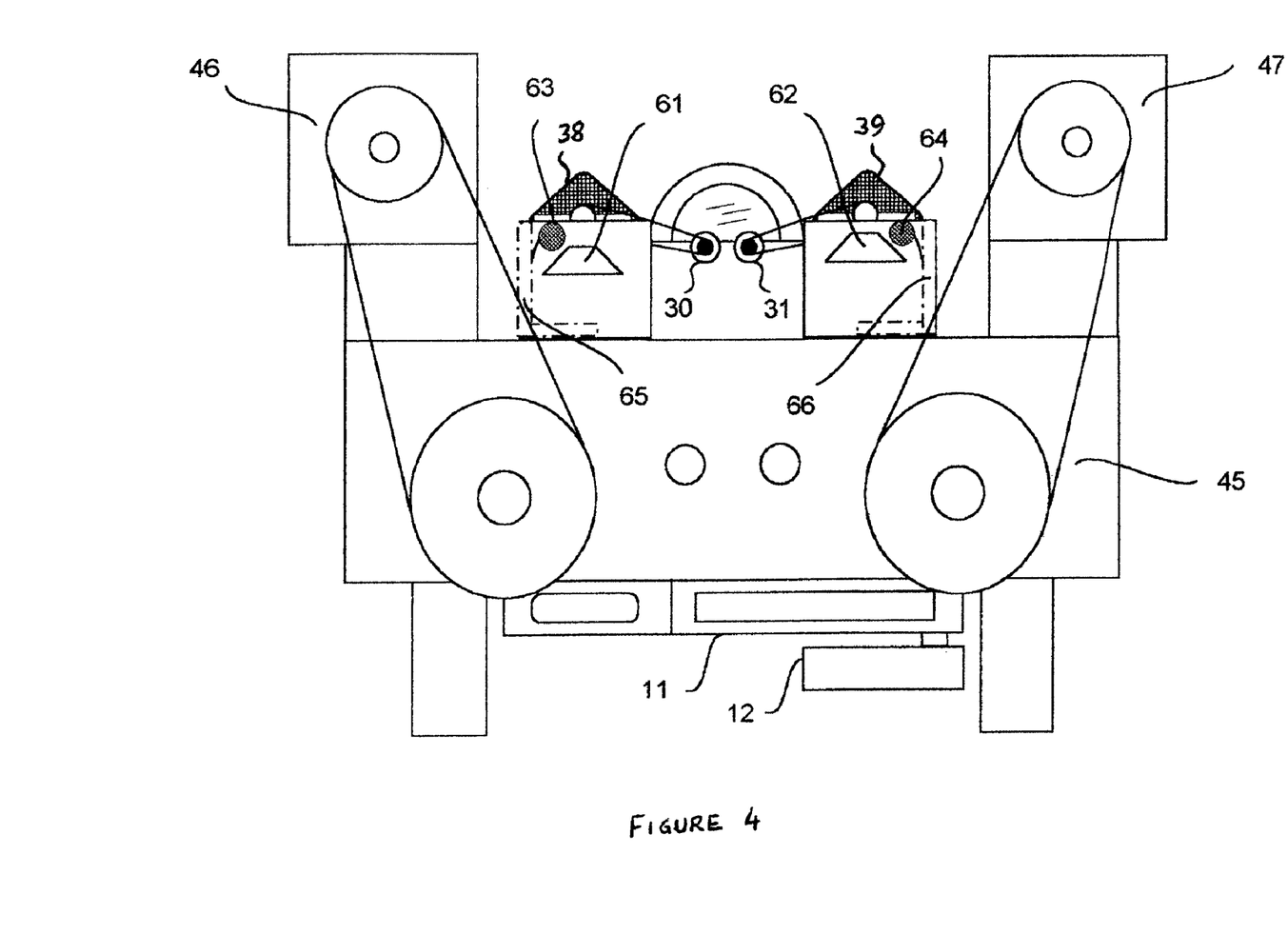
FIG. 4 is an internal rear elevation view of the subjective refractor of FIG. 1.
Figure 5:
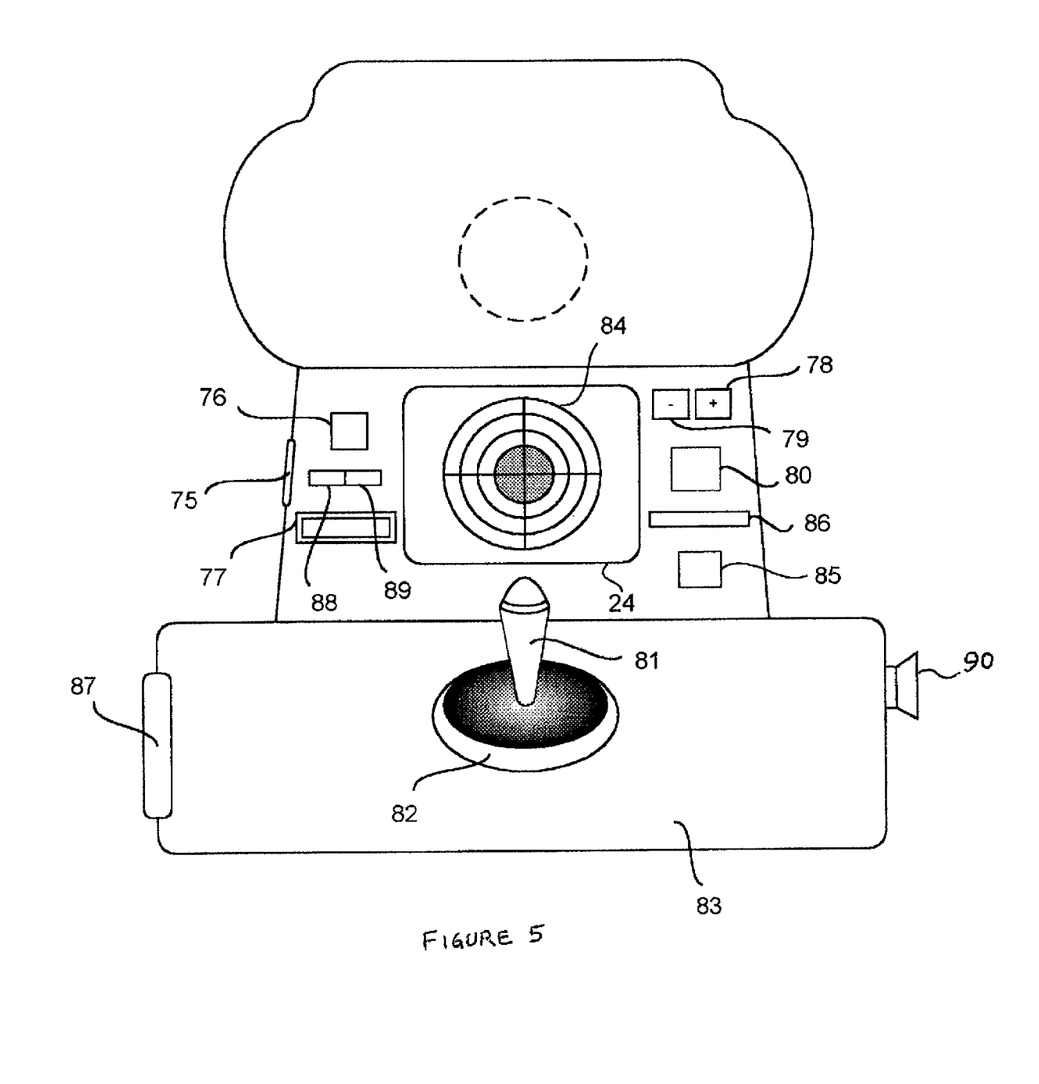
FIG. 5 is a top plan of the electronic boards of the apparatus of FIG. 1.
Figure 6:
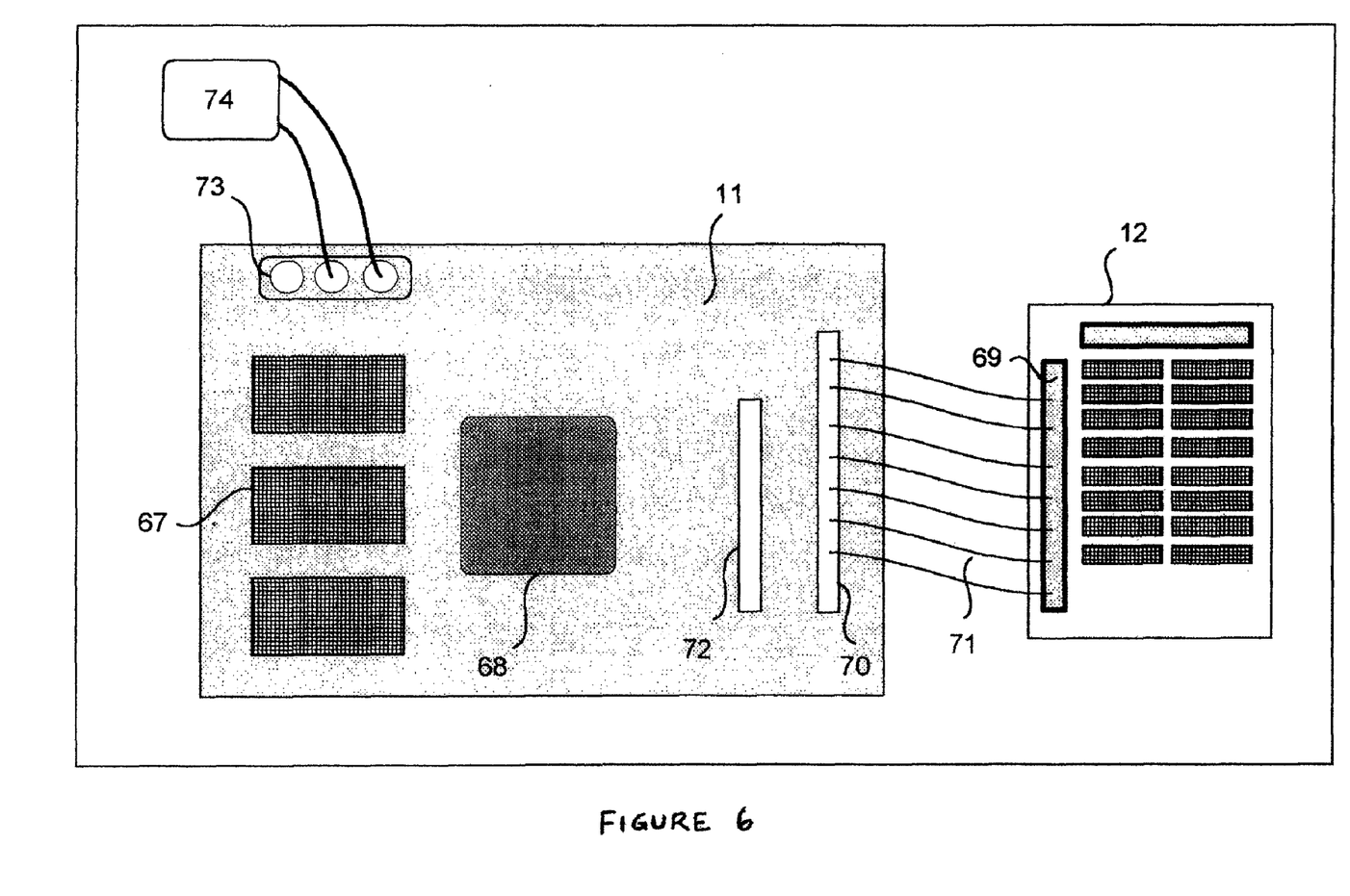
FIG. 6 is an external rear elevation view of the subjective refractor of FIG. 1.

As shown in FIG. 4 an internal rear elevation view of the apparatus, as the boot-up process or the re-calibration process continues, 'right side' rotatable drum (30) is rotated by way of right side rotational stepper motor (38), until a right side D-shaped actuator (61) engages a right side rotational limit switch (63). Similarly, left side rotatable drum (31) is rotated by way of left side rotational stepper motor (39), until a left side D-shaped actuator (62) engages left side rotational limit switch (64). The rotational limit switches are adjustably mounted upon brackets (65, 66), which are fixedly mounted upon the linearly movable carriages (40, 41). In an alternate embodiment, magnetic or optical shaft encoders or potentiometers may replace the actuators, rotational limits switches and mounting brackets, one for each rotational stepper motor, to allow the rotational position of each target to be calibrated electronically.

The rotational stepper motors (38, 39), and linear stepper motors (46, 47), are controlled by the system (11). The stepper motor driver board (12) is connected to the data management system (93) by way of stepper pin connectors (69, 70), and a data cable (71). The limit switches (56, 57, 63, 64) and subject input switches (8, 9, 10) connect to the data management system (93) at its input-output pin connector (72). Power is supplied to the data management system (93) at its electrical power connector (73), from a direct current power source (74).

FIG. 7 illustrates a system (11) in accordance with the teachings of the document. Based on subject input data in response to target presentations, reversal points will be obtained and stored in the memory (67). The range of these reversal points may be regarded as the range of each meridian. Based on the range for each meridian, an accommodative pattern detector and compensator (91,92) will act on the data for each meridian to minimize the effect of accommodation and produce meridional endpoint data. These meridional endpoint data are acted on by a formula programmed into the meridional synthesis module (95). The output of the meridional synthesis module is displayed as outputs for the examiner in the form of a monocular sphero-cylindrical optical endpoint.

The subject's response is conveyed to the system (11) that receives the input, and according to a set of pre-programmed instructions, moves the targets (3 and 4) either closer to or farther from the optical system (5) along a linear path. In an alternative embodiment, the stepper motor technology may be used in concert with a shaft encoder for the said stepper motors. Both alternative technologies provide electric feedback to the said system that specifies the position of the said targets at any moment in time.

For testing astigmatism refractive meridian orientations and their respective powers, three acceptable orientations might be 180 deg, 120 deg, and 60 deg. Other combinations of orientations may be equally acceptable, and the exact orientations are of little significance so long as they differ from one another by 45 deg or more. To accomplish this rotation, the system (11) would send signals to the stepper motor (12), which would cause the rotational motors (38, 39) to turn the rotational mechanics by an amount sufficient to rotate the targets (3, 4) by the desired amount. The same interactive procedure would then be used to refract the second meridian, and the outcome would be stored in the memory. Finally, refraction for a third orientation would be tested by further rotation of the two targets and the outcome would be stored in the memory.

If the eye has no astigmatism, the refraction of the eye is independent of target orientation. However, if the eye has astigmatism, refraction varies as a function of the orientation of the target. Whereas it may be possible to determine whether the eye has astigmatism by presenting a different kind of target e.g. one with radial lines at various orientations, such a procedure could necessitate intervention by an examiner. In an alternate embodiment such a radially oriented target may be provided in the optical system and be combined with a rotatable stenopaic slit, rotatable Scheiner disc, a rotatable astigmatic lens system, to facilitate determination of the far point of the eye.

The spectral bandwidth of the light illuminating the two targets should preferably be less than or equal to 160 nm at half peak luminance to minimize longitudinal and transverse chromatic aberration. Minimizing longitudinal chromatic aberration has the effect of reducing the tendency of the eye to accommodate when presented with a target nearer than the eye's far point. However, the use of light of bandwidth less than 20 nm is discouraged because it has the tendency to completely debilitate the focus-sensing chromatic mechanism of the eye thereby producing a spasm of accommodation in some individuals. The wavelength of peak luminance of a unimodal distribution will lie between 520 nm and 670 nm, and be preferably close to 600 nm. The use of 600 nm (580 nm or longer wavelength) has been shown to impair accommodation compared to wavelengths 570 nm or shorter. If the eye is refracted for light of wavelength 600 nm, 0.25 D minus lens power will be needed to focus 555 nm, the peak of the photopic luminous efficiency function.

The sequence of presentations of paired target focus positions may be designed so that if the subject tends to show a preference for near targets, the system will not immediately satisfy the subject's preference. Instead, the system will present targets that incrementally approach the subject's preference.

A preferred embodiment of the system for determining the refraction error of the eye in accordance with the teachings of the document is illustrated in FIG. 7. The subject indicates target preference using input switches (8, 9, and 10). The selection of a target or subject indication of target preference determines iterative focusing of targets by the focus altering means (94). Target preferences are stored in the memory module (67) in the form of "range of reversal" of each meridian. These range data are used by the accommodative pattern detector (91) to know whether the subject is over-accommodating. The accommodative pattern detector activates the accommodative pattern compensator (92) which works iteratively with the data management system (93) of the system (11) to control the stepper motor driver (12), or any other focus altering means. The iterative target focus is once again presented to the subject's eye (7) by way of the optical system (5). When the refraction for one meridian is completed, the targets are rotated by way or rotating mechanism (15, 16) to the next meridian. When a total of at least 2 meridians have been tested, the data are sent to the meridional synthesis module (95) which combines the refraction results from the meridians tested in concert with the data management system (93) to produce outputs in the form of a visual display (77), printer output (86), data output (87) and audio output (90).

Since the invention disclosed herein may be embodied in other specific forms without departing from the spirit or the general characteristics thereof, the embodiments described herein are to be considered in all respects illustrative and not restrictive. The scope of the invention is to be indicated by the appended claims rather than the foregoing description all changes which come within the meaning and range of equivalency of the claims are intended to be embraced therein.

What is claimed is:

1. A subjective refractor for determining refractive error of the eye comprising:
    an optical system configured to generate a predicted depth of focus of the eye and including an optical lens for presenting at least two targets to the eye, the two targets separated along the optical axis of the lens thereby providing a difference of focus between the at least two targets as observed by the eye and such that the difference of focus between the two targets is greater than the predicted depth of focus of the eye;
    means for indicating target preference from the presented targets; the target preference including an indication of target clarity;
    focus altering means for presenting again the at least two targets to the same eye such that the targets are dioptrically offset by a predetermined value in the direction of the preferred target based on the target preference; and
    means for determining refractive error of the eye on the basis of target preference.

2. The subjective refractor of claim 1, comprising a meridian altering mechanism for presenting the targets to the eye along at least two meridians of the eye.

3. The subjective refractor of claim 1, comprising means for presenting the targets to the eye along at least two orientations.

4. The subjective refractor of claim 1, wherein the optical system presents the targets simultaneously to one eye such that the targets are juxtaposed.

5. The subjective refractor of claim 1, wherein the optical system presents the targets successively to one eye such that the targets are presented sequentially.

6. The subjective refractor of claim 1, comprising focus altering means for altering focus of presented targets.

7. The subjective refractor of claim 1, wherein the optical system generates the predicted depth of focus based on the visual acuity and pupil diameter of the eye.

8. The subjective refractor of claim 1, wherein the light forming the targets has a bandwidth less than 160 nm and more than 20 nm such that the longitudinal chromatic aberration produced by the targets to the eye is reduced.

9. The subjective refractor of claim 1, wherein the target is comprised of stripes in substantially parallel orientation wherein the central stripe is smaller than the peripheral stripes to simulate a distant scene with geometric perspective in an effort to minimize near accommodation.

10. The subjective refractor of claim 1, comprising display means to display information pertaining to the refractor and the status of operation.

11. The subjective refractor of claim 1, wherein the targets are dioptrically offset by a predetermined diopter value in the direction of the preferred target.

12. The subjective refractor of claim 11, wherein the targets are dioptrically offset by half the predetermined diopter value in the direction of the preferred target when the preferred target is in the direction other than the direction of the preferred target of the preceding target preference indication.

13. A method of determining the refractive error of the eye comprising predicting the depth of focus of the eye; presenting at least two targets to the eye, the two targets being separated along the optical axis of a lens thereby providing a difference of focus between the at least two targets as observed by the eye and such that the difference of focus between the targets is greater than the predicted depth of focus of the eye, receiving target preference feedback, the target preference including an indication of target clarity; presenting again at least two targets to the same eye such that the targets are dioptrically offset by a predetermined diopter value in the direction of the preferred target based on the target preference feedback; and determining the refractive error based on the target preference feedback.

14. A system for determining the refractive error of the eye comprising:
   an optical system configured to generate a predicted depth of focus of the eye and for presenting at least two targets to the eye, the two targets providing a difference of focus as observed by the eye, the difference of focus between the targets being greater than the predicted depth of focus of the eye,
   a means for indicating target preference from the presented targets;
   a focus altering means altering the focus of presented targets; and
   a data management system for receiving target preference input and determining the refractive error of the eye.

15. The system of claim 14, wherein the targets are presented along at least two meridians of the eye.

16. The system of claim 15, comprising a meridian synthesis module for combining the refraction results for the at least two meridians.

* * * * *